United States Patent
Wen et al.

(10) Patent No.: US 10,438,340 B2
(45) Date of Patent: Oct. 8, 2019

(54) AUTOMATIC OPTICAL INSPECTION SYSTEM AND OPERATING METHOD THEREOF

(71) Applicant: Test Research, Inc., Taipei (TW)

(72) Inventors: Kuang-Pu Wen, Taipei (TW); Wen-Ming Wu, Taipei (TW); Chun-Yen Huang, Taipei (TW)

(73) Assignee: Test Research, Inc., Taipei (TW)

( * ) Notice: Subject to any disclaimer, the term of this patent is extended or adjusted under 35 U.S.C. 154(b) by 4 days.

(21) Appl. No.: 15/726,402

(22) Filed: Oct. 6, 2017

(65) Prior Publication Data

US 2018/0276811 A1    Sep. 27, 2018

Related U.S. Application Data

(60) Provisional application No. 62/474,084, filed on Mar. 21, 2017.

(51) Int. Cl.
| | | |
|---|---|---|
| *G06T 7/00* | (2017.01) | |
| *H04N 5/247* | (2006.01) | |
| *G01N 21/88* | (2006.01) | |
| *G01N 21/956* | (2006.01) | |
| G01N 21/95 | (2006.01) | |
| G01N 21/84 | (2006.01) | |

(52) U.S. Cl.
CPC ....... *G06T 7/0008* (2013.01); *G01N 21/8851* (2013.01); *G01N 21/956* (2013.01); *H04N 5/247* (2013.01); G01N 21/9501 (2013.01); G01N 2021/845 (2013.01); G01N 2021/8867 (2013.01); G01N 2021/9513 (2013.01); G01N 2021/95638 (2013.01); G01N 2201/0484 (2013.01); G06T 2207/30141 (2013.01); G06T 2207/30148 (2013.01)

(58) Field of Classification Search
CPC ......... G06T 7/0008; G06T 2207/30141; G06T 2207/30148; H04N 5/247; G01N 21/956; G01N 21/9501; G01N 2021/95638; G01N 2201/0484; G01N 2021/845
USPC ........................................... 348/92
See application file for complete search history.

(56) References Cited

U.S. PATENT DOCUMENTS

| | | | | | |
|---|---|---|---|---|---|
| 4,764,969 | A | * | 8/1988 | Ohtombe | ........... G01N 21/9501 348/128 |
| 6,178,257 | B1 | * | 1/2001 | Alumot | .................. G01N 21/94 382/145 |

(Continued)

FOREIGN PATENT DOCUMENTS

| | | |
|---|---|---|
| EP | 0179309 B1 | 9/1991 |
| EP | 1582863 A1 | 10/2005 |

(Continued)

*Primary Examiner* — Marnie A Matt
(74) *Attorney, Agent, or Firm* — CKC & Partners Co., LLC

(57) ABSTRACT

An automatic optical inspection system includes a first AOI machine and a second AOI machine, and the second AOI machine is electrically connected to the first AOI machine. The first AOI machine is configured to use a first resolution to inspect an object, so as to detect a possible defective region(s) of the object. The second AOI machine is configured to use a second resolution higher than the first resolution of the first AOI machine to inspect within the possible defective region(s) only, so as to detect whether there is/are any defect(s) within the possible defective region(s) of the object.

12 Claims, 4 Drawing Sheets

(56) References Cited

U.S. PATENT DOCUMENTS

| | | | |
|---|---|---|---|
| 2005/0072945 A1* | 4/2005 | Fukazawa | G01N 21/956 250/559.45 |
| 2007/0165939 A1* | 7/2007 | Savareigo | G01N 21/956 382/145 |
| 2008/0079931 A1 | 4/2008 | Lim et al. | |
| 2008/0204738 A1 | 8/2008 | Schupp et al. | |

FOREIGN PATENT DOCUMENTS

| | | |
|---|---|---|
| JP | 2000266691 A | 9/2000 |
| JP | 2009150718 A | 7/2009 |
| JP | 2014062837 A | 4/2014 |
| TW | 201415011 A | 4/2014 |
| TW | I468672 B | 1/2015 |

* cited by examiner

AUTOMATIC OPTICAL INSPECTION SYSTEM AND OPERATING METHOD THEREOF

RELATED APPLICATIONS

This application claims priority to U.S. Provisional Application Ser. No. 62/474,084, filed Mar. 21, 2017, which is herein incorporated by reference.

BACKGROUND

Field of Invention

The present invention relates to an automatic optical inspection system and an operating method thereof.

Description of Related Art

In the field of automatic inspection, the meaning of Zero Escape is to find out all defects, while it of Zero False Call is to exclude the actually normal products out of the inspected defects. Due to the conflict under the structure of single inspection between Zero Escape and Zero False Call, the conventional automatic single-machine-single-specification inspection cannot fulfill these two criteria simultaneously.

A conventional method uses fully- or semi-manual (with machine) to verify the inspected results for achieving the target of Zero Escape as much as possible, and then eliminates the normal products out of inspected defects manually, still, for the Zero False Call purpose.

However, human-dependent verification has its drawbacks of uncertainties, such as unpredictability, unverifiability, unrecordability and low repeatability. These unstable factors cause the manually verification inspection process unable to be integrated into the trend of fully-automatic, effective, and efficient productivity frame of Industry 4.0 with big data applications.

SUMMARY

The following presents a simplified summary of the disclosure in order to provide a basic understanding to the reader. This summary is not an extensive overview of the disclosure and it does not identify key/critical components of the present invention or delineate the scope of the present invention. Its sole purpose is to present some concepts disclosed herein in a simplified form as a prelude to the more detailed description that is presented later.

According to embodiments of the present disclosure, the present disclosure provides an automatic optical inspection system and an operating method thereof, to solve or circumvent aforesaid problems and disadvantages in the related art.

An embodiment of the present disclosure is related to an automatic optical inspection system including a first AOI machine and a second AOI machine, and the second AOI machine is electrically connected to the first AOI machine. The first AOI machine is configured to use a first resolution to inspect an object, so as to detect any possible defective region(s) of the object. The second AOI machine is configured to use a second resolution different from the first one to inspect the possible defective region(s) of the object detected by the first AOI machine only, so as to detect whether there is/are any defect(s) within the possible defective region(s) of the object, where the second resolution is higher than the first resolution.

In one embodiment, while there is/are any defect(s) within the possible defect region(s) of the object inspected by the second AOI machine, the object is determined as an unacceptable object by the second AOI machine.

In one embodiment, while there is no defect within the possible defect region(s) of the object inspected by the second AOI machine, the object is determined as an acceptable object by the second AOI machine.

In one embodiment, while there is no possible defective region of the object inspected by the first AOI machine, the object will be allowed to pass through the second AOI machine directly without being inspected.

In one embodiment, the automatic optical inspection system further includes a set of transportation device module(s) configured to transport the object from the first AOI machine to the second AOI machine.

In one embodiment, the first AOI machine comprises: a first set of motion device module(s) configured to carry the object; a first set of optical module(s) configured to capture a first set of image(s) based on the first resolution from the object on the first set of motion device module(s); a first set of processor(s) configured to perform a set of computation(s) on the first set of image(s), so as to recognize the possible defective region(s) of the object; and a transmitter configured to transmit data associated with the possible defective region(s) of the object to the second AOI machine.

In one embodiment, the second AOI machine comprises: a receiver configured to receive the data associated with the possible defective region(s) of the object; a second set of motion device module(s) configured to carry the object; a second set of optical module(s) configured to capture a second set of image(s) based on the second resolution higher than the first resolution from the possible defective region(s) of the object on the second set of motion device modules(s); and a second set of processor(s) configured to perform a set of computation(s) on the second set of image(s), so as to recognize whether there is/are any defect(s) within the possible defective region(s) of the object.

In one embodiment, the first set of image(s) captured by the first AOI machine can be any formats of image of the object, and so is the second set of image(s) captured by the second AOI machine within the possible defective region(s) of the object.

In one embodiment, the formats can be gray-level, colored, HDR (high dynamic range), raw, compressed, one-dimensional, two-dimensional, three-dimensional, or any other possible image formats.

In one embodiment, the object is a printed circuit board, a semiconductor wafer, a display panel or the like.

Another embodiment of the present disclosure is related to an operating method of an AOI system including a first AOI machine and a second AOI machine, and the operating method includes steps of utilizing the first AOI machine to use a first resolution to inspect an object, so as to detect a possible defective region(s) of the object; and utilizing the second AOI machine to use a second resolution higher than the first resolution of the first AOI machine to inspect within the possible defective region(s) only, so as to detect whether there is/are any defect(s) within the possible defective region(s) of the object.

In one embodiment, while there is/are any defect(s) within the possible defect region(s) of the object, the object is determined as an unacceptable object by the second AOI machine.

In one embodiment, while there is no any defect within the possible defect region(s) of the object, the object is determined as an acceptable object by the second AOI machine.

In one embodiment, while there is no any possible defective region(s) of the object detected by the first AOI machine, the object will be allowed to pass through the second AOI machine directly without being inspected.

In one embodiment, the operating method further includes utilizing a set of transportation device module(s) to transport the object from the first AOI machine to the second AOI machine.

In one embodiment, the step of utilizing the first AOI machine includes: carrying the object by a first set of motion device module(s) of the first AOI machine; capturing a first set of image(s) based on a first resolution from the object on the first set of motion device module(s); performing a set of computation(s) on the first set of image(s), so as to recognize whether there is/are any possible defective region(s) of the object; and transmitting data associated with the possible defective region(s) of the object to the second AOI machine.

In one embodiment, the step of utilizing the second AOI machine includes: receiving the data associated with the possible defective region(s) of the object; carrying the object by a second set of motion device module(s) of the second AOI machine; capturing a second set of image(s) based on the second resolution higher than the first resolution of the first AOI machine within the possible defective region(s) of the object on the second set of motion device module(s); and performing a set of computation(s) on the second set of image(s), so as to recognize whether there is/are any defect(s) within the possible defective region(s) of the object.

In one embodiment, the first set of image(s) captured by the first AOI machine can be any formats of image, and so is the set of image(s) captured by the second AOI machine within the possible defective region(s) of the object.

In one embodiment, the formats can be gray-level, colored, HDR (high dynamic range), raw, compressed, one-dimensional, two-dimensional, three-dimensional, or any other possible image formats.

In one embodiment, the object is a printed circuit board, a semiconductor wafer, a display panel or the like.

In view of the above, the present disclosure provides the AOI system with Zero False Call and Zero Escape, thereby eliminating the costs and uncertainties of human-dependent verifications. Moreover, the AOI system brings the process of the first and second AOI machines into the structure of Industry 4.0 with big data applications.

Many of the attendant features will be more readily appreciated, as the same becomes better understood by reference to the following detailed description considered in connection with the accompanying drawings.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
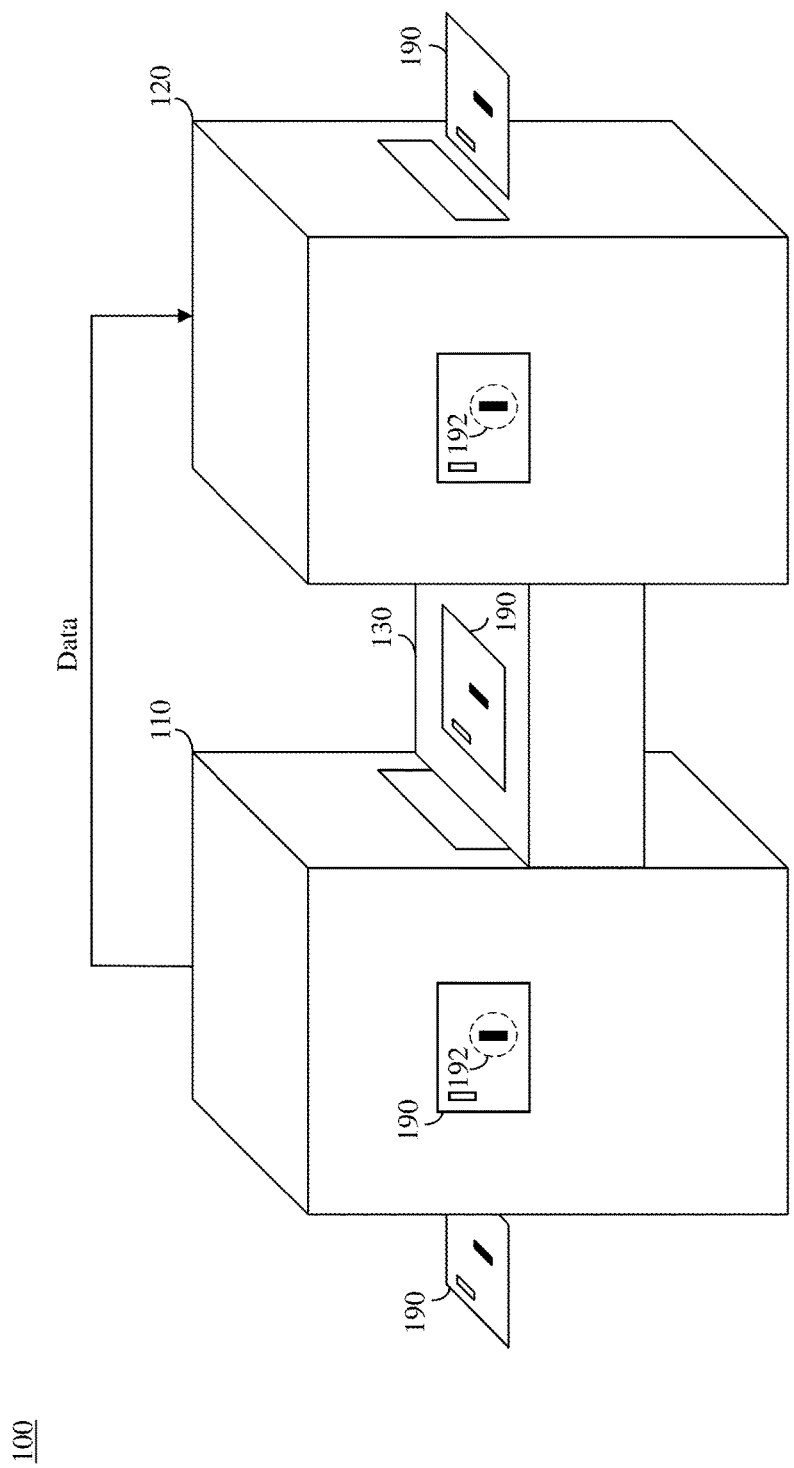
FIG. 1 is a schematic diagram illustrating an automatic optical inspection (AOI) system according to some embodiments of the present disclosure.

Reference will now be made in detail to the present embodiments of the invention, examples of which are illustrated in the accompanying drawings. Wherever possible, the same reference numbers are used in the drawings and the description to refer to the same or like parts.

As used in the description herein and throughout the claims that follow, the meaning of "a", "an", and "the" includes reference to the plural unless the context clearly dictates otherwise. Also, as used in the description herein and throughout the claims that follow, the terms "comprise or comprising", "include or including", "have or having", "contain or containing" and the like are to be understood to be open-ended, i.e., to mean including but not limited to. As used in the description herein and throughout the claims that follow, the meaning of "in" includes "in" and "on" unless the context clearly dictates otherwise.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a schematic diagram illustrating an automatic optical inspection system 100 according to some embodiments of the present disclosure. As shown in FIG. 1, the automatic optical inspection system 100 includes a first AOI machine 110, a second AOI machine 120 and a set of transportation device module(s) 130. For example, the first AOI machine 110 may be a 3D solder paste inspection (SPI) machine, or the like. The second AOI machine 120 may be an automatic re-inspection machine. The set of transportation device module(s) 130 may be a set of robotic arm(s), a track, a jig, a rail guided vehicle (RGV), an automatic guided vehicle (AGV), an automatic transportation device or the like.

Structurally, the second AOI machine 120 is electrically connected to the first AOI machine 110, so that the first AOI machine 110 can transmit data to the second AOI machine 120. In addition, the set of transportation device module(s) 130 physically connects the first AOI machine 110 and the second AOI machine 120, so that the set of transportation device module(s) 130 can transport an object 190 from the first AOI machine 110 to the second AOI machine 120. In one embodiment, the object 190 is a printed circuit board. In an alternative one embodiment, the object 190 is a semiconductor wafer, a display panel or the like.

In practice, the first AOI machine 110 is configured to use a first resolution (e.g., a relatively low resolution) to inspect the object 190, so as to detect a possible defective region(s) 192 of the object 190. Since the first resolution is a relatively low resolution, the first AOI machine 110 can fast identify the possible defective region(s) 192 with a possible defective type for Zero Escape, and the possible defective region(s) 192 in the object 190 may be evaluated as being real or false defects for Zero False Call. For example, the real defect includes, for example, conductors having various protrusions some of which may result short circuits, copper splashes, certain missing features, conductors having a severe nick, a non-localized improper width, breaks along conductors or the like.

Accordingly, the second AOI machine 120 is configured to use a second resolution (e.g., a relatively high resolution) to inspect the possible defective region(s) 192 only rather than a whole of the object 190, so as to reduce the cycle time of this re-inspection. Since the second resolution is a relatively high resolution, the second AOI machine 120 can be used to automatically and accurately detect whether there is/are any defect(s) (i.e., a real defect(s)) within the possible defective region(s) 192 of the object 190, thereby accomplishing Zero False Call without the manual verification. In some embodiments, the second resolution is higher than the first resolution. For example, the second resolution is 2-3 um, the first resolution is 10 um, but the present disclosure is not limited thereto.

While there is/are any defect(s) within the possible defect region(s) of the object 190 detected by the second AOI machine 120, the object 190 is determined as an unacceptable one by the second AOI machine 120. While there is/are no defect(s) within the possible defect region(s) 192 of the object 190 detected by the second AOI machine 120, the object 190 is determined as an acceptable object by the second AOI machine 120.

Moreover, while there is no possible defective region of the object 190 detected by the first AOI machine, the object 190 will be allowed to pass through the second AOI machine 120 directly without being inspected.

Figure 2:
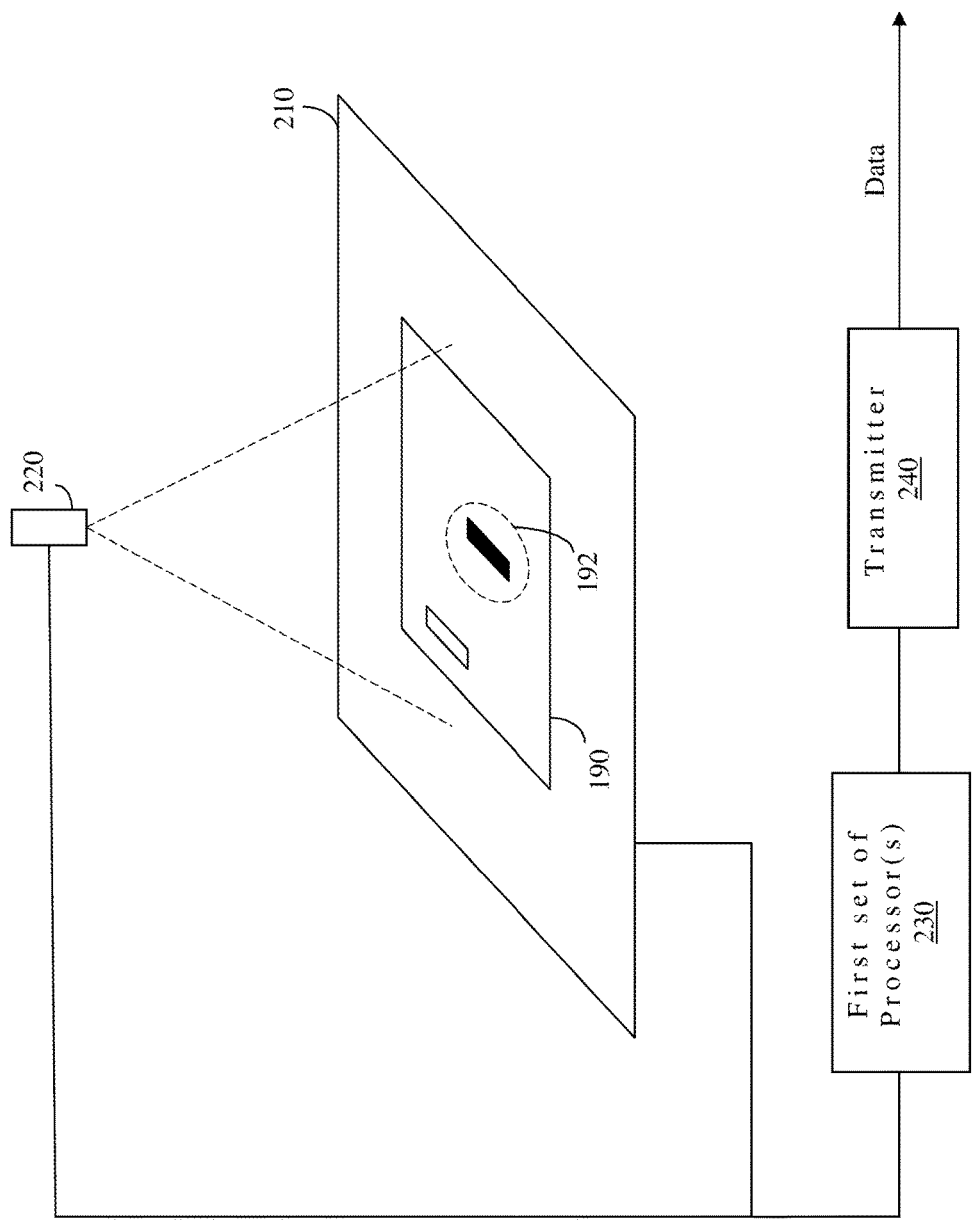
FIG. 2 is a schematic diagram illustrating a first AOI machine according to some embodiments of the present disclosure.

FIG. 2 is a schematic diagram illustrating the first AOI machine 110 according to some embodiments of the present disclosure. As shown in FIG. 2, the first AOI machine 110 includes a first set of motion device module(s) 210, a first set of optical module(s) 220, a first set of processor(s) 230 and a transmitter 240.

Structurally, the first set of processor(s) 230 is electrically connected to the first set of motion device module(s) 210, the first set of optical module(s) 220 and the set of transmitter(s) 240. For example, the first set of motion device module(s) 210 may be a set of robotic arm(s), a XY table, a XY stage, a XYZ table, and a set of conveyer(s) or other axis controllers. The first set of optical module(s) 220 may include a set of lens (e.g., a set of telecentric lens, a set of microscope lens, etc.) and a set of image sensor(s) (e.g., a set of 2D image data sensor(s), a set of 3D height data sensor(s), etc.), where the set of 2D image data sensor(s) can capture mono images, color images, infrared (IR) images or the like, and the set of 3D height data sensor(s) can capture laser image data, pattern, depth-from-focus (DFF) data or the like. The first set of processor(s) 230 may be a set of central processing unit(s) (CPU), a set of microcontroller(s) or the like. The transmitter 240 may be a set of wired and/or wireless transmitter(s) that directly or indirectly communicates with the second AOI machine 120.

In practice, the first set of motion device module(s) 210 is configured to carry the object 190. The first set of optical module(s) 220 is configured to capture a first set of image(s) based on the first resolution from the object 190 on the first set of motion device module(s) 210. The first set of processor(s) 230 is configured to perform a set of computation(s) on the first set of image(s), so as to recognize the possible defective region(s) 192 of the object 190. The set of transmitter(s) 240 is configured to transmit data associated with the possible defective region(s) 192 of the object 190 to the second AOI machine.

Figure 3:
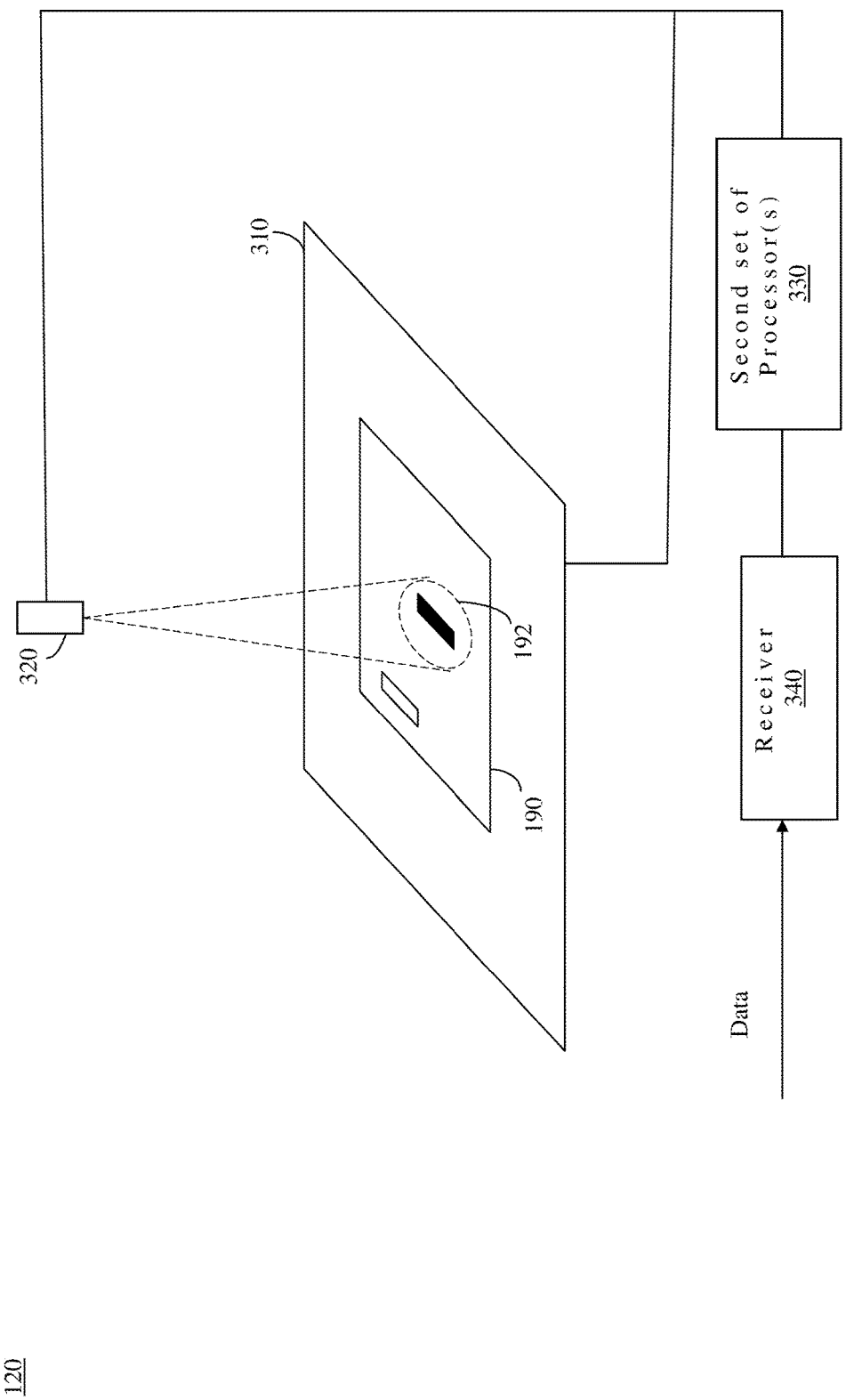
FIG. 3 is a schematic diagram illustrating a second AOI machine according to some embodiments of the present disclosure.

FIG. 3 is a schematic diagram illustrating the second AOI machine 120 according to some embodiments of the present disclosure. As shown in FIG. 3, the second AOI machine 120 includes a second set of motion device module(s) 310, a second set of optical module(s) 320, a second set of processor(s) 330 and a receiver 340.

Structurally, the second set of processor(s) 330 is electrically connected to the set of (s) second motion device module(s) 310, the second set of optical module(s) 320 and the receiver 340. For example, the second set of motion device module(s) 310 may be a set of robotic arm(s), a XY table, a XY stage, a XYZ table, and a set of conveyer(s) or other axis controllers. The second set of optical module(s) 320 may include a set of lens (e.g., a set of telecentric lens, a set of microscope lens, etc.) and a set of image sensor(s) (e.g., a set of 2D image data sensor(s), a set of 3D height data sensor(s), etc.), where the set of 2D image data sensor(s) can capture mono images, color images, infrared (IR) images or the like, and the set of 3D height data sensor(s) can capture laser image data, pattern, depth-from-focus (DFF) data or the like. The second set of processor(s) 330 may be a set central processing unit(s) (CPU), a set of microcontroller(s) or the like. The receiver 340 may be a set of wired and/or wireless receiver(s) that directly or indirectly communicates with the transmitter 240 of the first AOI machine 110.

In practice, the receiver 340 is configured to receive the data associated with the possible defective region(s) 192 of the object 190 from the transmitter 240. The second set of motion device module(s) 310 is configured to carry the object 190. The second set of optical module(s) 320 is configured to capture a second set of image(s) based on the second resolution higher than the first resolution captured from the possible defective region(s) 192 of the object 190 on the second set of motion device module(s) 310. The second set of processor(s) 330 is configured to perform a set of computation(s) on the second set of image(s), so as to recognize whether there is/are any defect(s) within the possible defective region(s) 192 of the object 190.

In practice, the receiver 340 is configured to receive the data associated with the possible defective region(s) 192 of the object 190 from the transmitter 240. The second set of motion device module(s) 310 is configured to carry the object 190. The second set of optical module(s) 320 is configured to capture a second set of image(s) based on the second resolution higher than the first resolution captured from the possible defective region(s) 192 of the object 190 on the second set of motion device module(s) 310. The second set of processor(s) is configured to perform a set of computation(s) on the second set of image(s), so as to recognize whether there is/are any detect(s) within the possible defective region(s) 192 of the object 190.

In one embodiment, the first set of image(s) captured by the first AOI machine can be any formats of image, and so is the second set of image(s) captured by the second AOI machine within the possible defective region(s) of the object. In another embodiment, those formats can be gray-level, colored, HDR (high dynamic range), raw, compressed, one-dimensional, two-dimensional, three-dimensional, or any other possible image formats.

Figure 4:
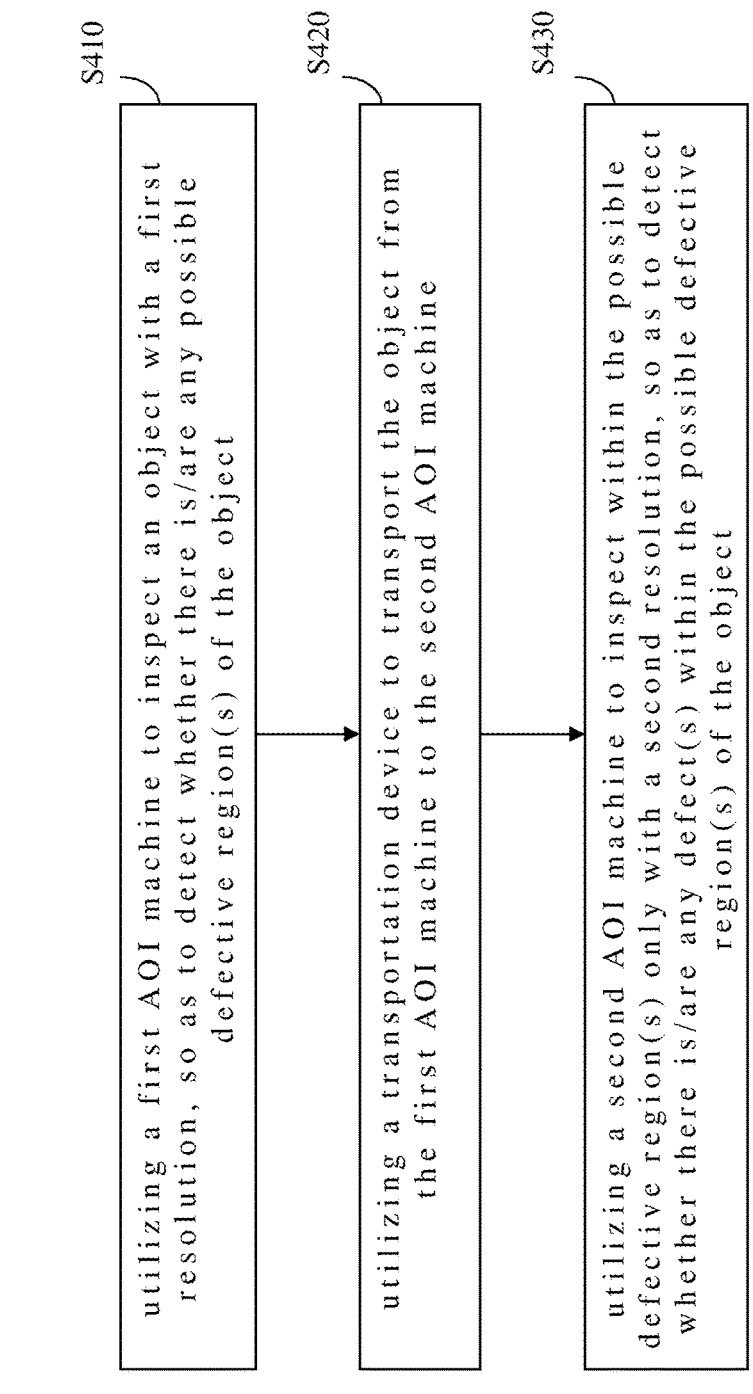
FIG. 4 is a flow chart illustrating an operating method of an AOI system according to some embodiments of the present disclosure.

For a more complete understanding of operating the AOI system 100, referring FIGS. 1-4, FIG. 4 is a flow chart illustrating an operating method 400 of an AOI system 100 according to some embodiments of the present disclosure. As shown in FIG. 4, the operating method 400 includes operations S410, S420 and S430. However, as could be appreciated by persons having ordinary skill in the art, for the steps described in the present embodiment, the sequence in which these steps is performed, unless explicitly stated otherwise, can be altered depending on actual needs; in certain cases, all or some of these steps can be performed concurrently.

In operation S410, the first AOI machine 110 is utilized to inspect an object with a first resolution, so as to detect a possible defective region(s) 192 of the object 190. Specifically, the object 190 is carried by a first set of motion device module(s) 210 of the first AOI machine 110, a first set of image(s) is captured based on the first resolution from the object 190 on the first set of motion device module(s) 210, a set of computation(s) is performed on the first set of image(s), so as to recognize the possible defective region(s) 192 of the object 190, and data associated with the possible defective region(s) 192 of the object 190 are transmitted to the second AOI machine 120.

In operation S420, the set of transportation device module(s) 130 is utilized to transport the object 190 from the first AOI machine 110 to the second AOI machine 120.

In operation S430, the second AOI machine 120 is utilized to use a second resolution to inspect within the possible defective region(s) 192 only, so as to detect whether there is/are any defect(s) within the possible defective region(s) 192 of the object 190, where the second resolution is higher than the first resolution. Specifically, the data associated with the possible defective region(s) of the object are received from the first AOI machine 110, the object 190 is carried by the a second set of motion device module(s) 310 of the second AOI machine 120, a second image(s) is captured based on the second resolution from the possible defective region(s) 192 of the object 190 on the second set of motion device module(s) 310, and a set of computation(s) is performed on the second set of image(s), so as to recognize whether there is/are any defect(s) within the possible defective region(s) 192 of the object 190.

In the operating method 400, while there is/are any defect(s) within the possible defect region(s) 192 of the object 190 detected by the second AOI machine, the object 190 is determined as an unacceptable object by the second AOI machine 120.

In the operating method 400, while there is no any defect within the possible defective region(s) 192 of the object 190 detected by the second AOI machine 120, the object 190 is determined as an acceptable object by the second AOI machine 120.

In the operating method 400, while there is no any possible defective region 192 of the object 190 detected by the first AOI machine 110, the object 190 will be allowed to pass through the second AOI machine 120 directly without being inspected.

In view of the above, the present disclosure provides the AOI system 100 with Zero False Call and Zero Escape, thereby eliminating the costs and uncertainties of human-dependent verifications. Moreover, the AOI system 100 brings the process of first and second AOI machines 110 and 120 into the structure of Industry 4.0 with big data applications.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. An automatic optical inspection (AOI) system, comprising:
   a first AOI machine configured to use a first resolution to inspect a printed circuit board, so as to detect whether there is any possible defective region of the printed circuit board; and
   a second AOI machine electrically connected to the first AOI machine, the second AOI machine configured to use a second resolution to inspect within the possible defective region only, so as to detect whether there is any defect within the possible defective region of the printed circuit board, wherein the second resolution is higher than the first resolution,
   wherein if there is no possible defective region of the printed circuit board detected by the first AOI machine, the printed circuit board is allowed to pass through the second AOI machine directly without being inspected,
   wherein the first AOI machine comprises:
      a first motion device module configured to carry the printed circuit board;
      a first optical module configured to capture a first image based on the first resolution from the printed circuit board on the first motion device module;
      a first processor configured to perform a computation on the first image, so as to recognize the possible defective region of the printed circuit board; and
      a transmitter configured to transmit data associated with the possible defective region of the printed circuit board to the second AOI machine directly,
   wherein the second AOI machine comprises:
      a receiver configured to receive the data associated with the possible defective region of the printed circuit board from the transmitter of the first AOI machine directly;
      a second motion device module configured to carry the printed circuit board;
      a second optical module configured to capture a second image based on the second resolution from the possible defective region of the printed circuit board on the second motion device module; and
      a second processor configured to perform computation on the second image, so as to recognize whether there is the any defect within the possible defective region of the printed circuit board.

2. The automatic optical inspection system of claim 1, wherein if there is a defect within the possible defect region of the printed circuit board, the printed circuit board is determined as an unacceptable printed circuit board by the second AOI machine.

3. The automatic optical inspection system of claim 1, wherein if there is no defect within the possible defect region of the printed circuit board, the printed circuit board is determined as an acceptable printed circuit board by the second AOI machine.

4. The automatic optical inspection system of claim 1, further comprising:

a transportation device module configured to transport the printed circuit board from the first AOI machine to the second AOI machine.

5. The automatic optical inspection system of claim 1, wherein the first image captured by the first AOI machine is any format of image of the printed circuit board, and the second set of image captured by the second AOI machine is within the possible defective region of the printed circuit board.

6. The automatic optical inspection system of claim 5, wherein the format can be gray-level, colored, HDR (high dynamic range), raw, compressed, one-dimensional, two-dimensional, or three-dimensional.

7. An operating method of an AOI system including a first AOI machine and a second AOI machine, and the operating method comprising:
    utilizing the first AOI machine to use a first resolution to inspect a printed circuit board, so as to detect a possible defective region of the printed circuit board, wherein utilizing the first AOI machine comprises: carrying the printed circuit board by a first motion device module of the first AOI machine; utilizing a first optical module of the first AOI machine for capturing a first image based on the first resolution from the printed circuit board on the first motion device module; utilizing a first processor of the first AOI machine for performing computation on the first image, so as to recognize the possible defective region of the printed circuit board; and utilizing a transmitter of the first AOI machine for transmitting data associated with the possible defective region of the printed circuit board to the second AOI machine directly; and
    utilizing the second AOI machine to use a second resolution to inspect within the possible defective region only, so as to detect whether there is any defect within the possible defective region of the printed circuit board, wherein the second resolution is higher than the first resolution, wherein utilizing the second AOI machine comprises: receiving the data associated with the possible defective region of the printed circuit board from the transmitter of the first AOI machine directly; carrying the printed circuit board by a second motion device module of the second AOI machine; utilizing a second optical module of the second AOI machine for capturing a second image based on the second resolution from the possible defective region of the printed circuit board on the second motion device module; and utilizing a second processor of the second AOI machine for performing a computation on the second image, so as to recognize whether there is any defect within the possible defective region of the printed circuit board,
    wherein if there is no possible defective region of the printed circuit board detected by the first AOI machine, the printed circuit board is allowed to pass through the second AOI machine directly without being inspected.

8. The operating method of claim 7, wherein if there is a defect within the possible defect region of the printed circuit board, the printed circuit board is determined as an unacceptable printed circuit board by the second AOI machine.

9. The operating method of claim 7, wherein if there is no defect within the possible defect region of the printed circuit board, the printed circuit board is determined as an acceptable printed circuit board by the second AOI machine.

10. The operating method of claim 7, further comprising:
    utilizing a transportation device module to transport the printed circuit board from the first AOI machine to the second AOI machine.

11. The automatic optical inspection system of claim 7, wherein the first image captured by the first AOI machine is any format of image of the printed circuit board, and the second image captured by the second AOI machine is within the possible defective region of the printed circuit board.

12. The automatic optical inspection system of claim 11, wherein the format is gray-level, colored, HDR (high dynamic range), raw, compressed, one-dimensional, two-dimensional, or three-dimensional.

\* \* \* \* \*